United States Patent [19]

Lassen

[11] Patent Number: 4,605,405
[45] Date of Patent: Aug. 12, 1986

[54] DYNAMICALLY MOVEABLE NAPKIN

[75] Inventor: Frederich O. Lassen, Winnebago County, Wis.

[73] Assignee: Kimberly-Clark Corporation, Neenah, Wis.

[21] Appl. No.: 536,034

[22] Filed: Sep. 26, 1983

[51] Int. Cl.$^4$ ............................................. A61F 13/16
[52] U.S. Cl. .................................. 604/389; 604/385.R 604/386; 604/390
[58] Field of Search ........ 604/366, 370, 385, 389–399, 604/400–402, 386–388

[56] References Cited

U.S. PATENT DOCUMENTS

| 929,166 | 7/1909 | Plamondon | 604/400 |
| 3,315,677 | 4/1967 | Tyrrell | 604/387 |
| 3,420,236 | 1/1969 | De Woskin | 604/398 |
| 3,455,303 | 7/1969 | Wilson | 604/400 |
| 3,967,623 | 7/1976 | Butterworth et al. | 604/381 |

Primary Examiner—C. Fred Rosenbaum
Assistant Examiner—Sherri E. Vinyard
Attorney, Agent, or Firm—Paul A. Leipold; Donald L. Traut; J. J. Duggan

[57] ABSTRACT

A sanitary napkin is provided with a positioning strap in slideable contact with a low friction baffle which is attached to the bottom of the napkin. The contact between the positioning strap and the baffle is maintained by a retention strap attached to the napkin which encircles the positioning strap. Attachment means are provided at each end of the positioning strap on the surface opposite that in slidable contact with the baffle.

8 Claims, 4 Drawing Figures

DYNAMICALLY MOVEABLE NAPKIN

FIELD OF THE INVENTION

The invention relates to a sanitary napkin and particularly a sanitary napkin which is dynamically moveable during use.

BACKGROUND OF THE INVENTION

Sanitary napkins have been conventionally held in place by the user by means either of a belt which is designed to attach to tabs extending beyond the ends of a napkin or, by pressure sensitive adhesive which attaches directly to the wearer's undergarment. These adhesively attached "tabless" napkins are virtually the only type of napkins currently sold.

Tabless napkins have the advantage of providing relatively easy and simple attachment without the need for a separate belt. Unfortunately, once the tabless napkins are positioned in the undergarment of the wearer they tend to stay in the same position. Sanitary napkins are not elastic and when the wearer is in motion, the sanitary napkin is not. The result is rubbing and irritation where the wearer's flesh slides along the outer surface of the napkin. Alternatively, the napkin can be distorted or unattached due to the motion of the wearer which produces napkin failure.

Sanitary napkins have also been made with extensions usually as part of an attachment system.

U.S. Pat. No. 2,964,040 discloses a tabbed sanitary napkin with a separate strip for tab attachment.

U.S. Pat. No. 3,688,771 discloses a sanitary napkin which can be used either as a tabbed or tabless napkin by utilizing the release strip as an extension for tabbed attachment.

U.S. Pat. No. 4,285,343 discloses a sanitary napkin having edge extensions which are designed to wrap around an overlap of the bottom crotch area of the wearer's panties and attach thereto.

None of these prior art napkins, however, provides for dynamic slideable movement of the napkin in response to wearer motion.

SUMMARY OF THE INVENTION

According to this invention a sanitary napkin is provided which allows for constrained longitudinal slideable movement of the napkin in response to wearer motion. This is accomplished by providing a sanitary napkin with a low friction baffle on the garment facing side thereof in slideable contact with a positioning strap also with a low friction surface. The positioning strap is adhesively attached at either one or both ends in the crotch area of the wearer's undergarment. In certain embodiments the contact between the positioning strap and the low friction baffle is maintained by a retaining strap attached at either side of the napkin and encircling the positioning strap.

DETAILED DESCRIPTION OF THE INVENTION AND DRAWINGS

The invention may be more readily understood by reference to the drawings in which.

Figure 1:
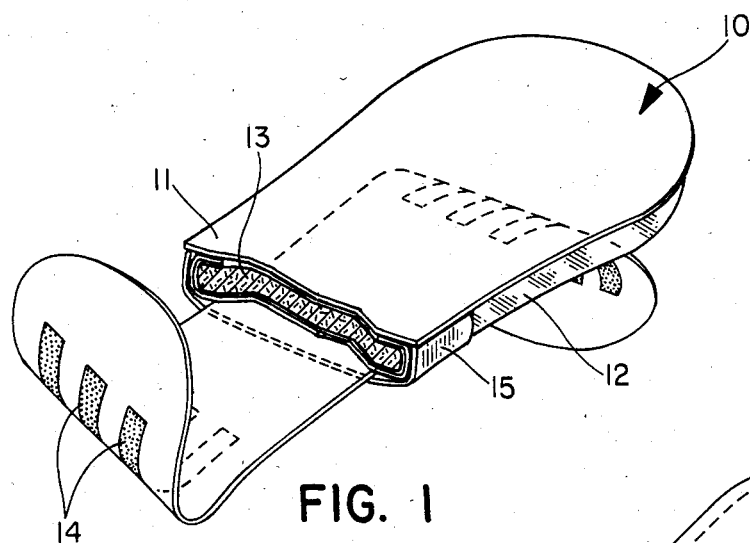
FIG. 1 is a perspective view partially in cross section showing the napkin of this invention positioned for attachment to the wearer's undergarment.
Figure 2:
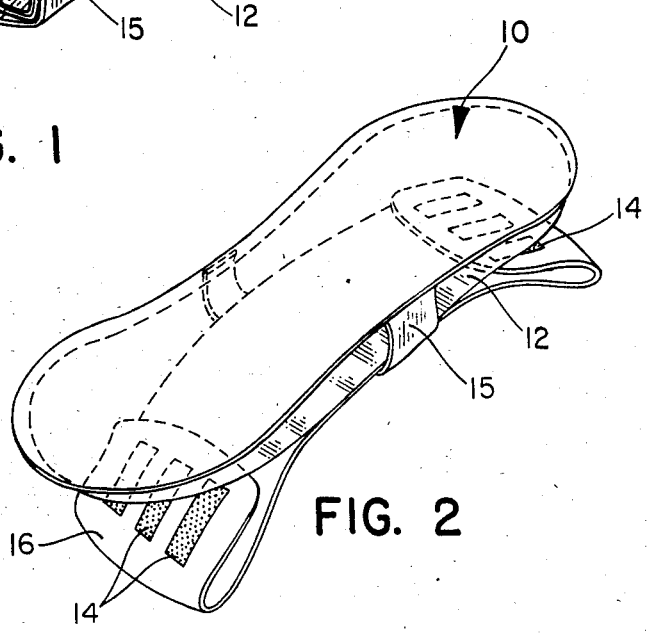
FIG. 2 is a perspective view of the embodiment shown in FIG. 1 prior to positioning.

Referring now to the drawings, as can be seen in FIGS. 1 and 2, a pad generally referred to at 10 contains a fluid permeable cover 11 positioned on the upper or body facing side of the napkin. A fluid impermeable baffle 12 is provided at least on the bottom or garment facing surface of the napkin, and, as shown in FIG. 1 extends along the sides of the napkin also. The combination of the cover 11 and baffle 12 surround an absorbent layer 13 which may be of any conventional construction as known in the art. The particular choice of absorbent is not part of this invention. A retention strap 15 is attached to the napkin sides approximately centrally with respect to the longitudinal axis of the napkin. A retention strap 15 is located so that one surface of the strap is adjacent the low friction baffle 12. The retention strap 15 encircles a portion of the positioning strap 16 but still allows relative movement of the low friction surface of the positioning strap 16 and the baffle 12. Attachment adhesive blocks 14 are positioned on the garment facing side of the positioning strap 16 and attach the positioning strap, and, necessarily the remainder of the napkin, to the garment of the wearer. The napkin is, therefore, free to slide along the positioning strap between the blocks of attachment adhesive in response to movement by the wearer. Because of this relatively free movement, the napkin itself will be less subject to distortion forces which act to distort the top surface of the napkin and provide for mispositioning of the napkin with respect to fluid discharge.

Because of the construction of this napkin, movement is limited primarily to the longitudinal direction with respect to the napkin axis and even that motion is limited by the positioning of the adhesive. Therefore, while the napkin can move slideably, that motion is limited to prevent the napkin from being positioned in such a way as to not absorb fluid.

As can be seen from FIG. 2, the napkin can be assembled so that the positioning strap 16 is folded upon itself allowing the baffle 12 to serve as a release liner for the adhesive attachment blocks 14. While adhesive attachment is the currently accepted and desirable means for attachment of the positioning strap, the attachment may be by other means as well. It is the location of the attachment which is important rather than the particular means chosen, as can be seen from the relative positioning of the component illustrated in FIG. 1.

Figures 3, 4:
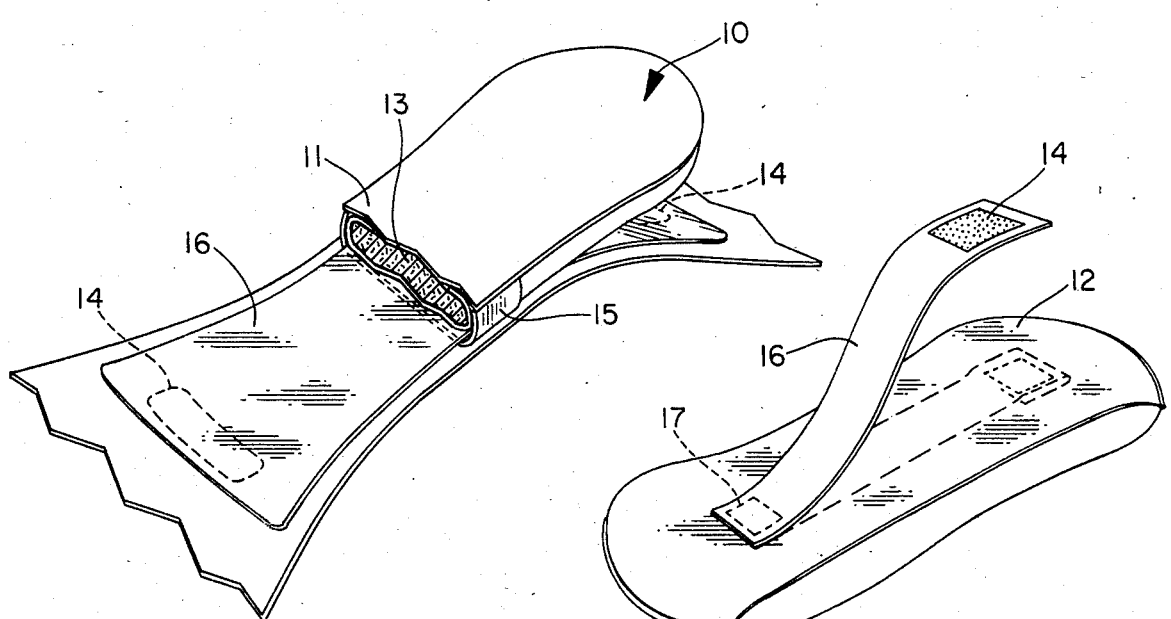
FIG. 3 is a perspective view partially in cross section of a second embodiment of the sanitary napkin of this invention.
FIG. 4 is a perspective view of a third embodiment of this invention.

A second embodiment of the invention is depicted at FIG. 3. The numbers corresponding to the components in FIGS. 1 and 2 are designated identically in FIG. 3. As can be seen in FIG. 3, a positioning strap which generally corresponds to the configurational profile of the crotch of the wearer's undergarments is utilized as the positioning strap 16. The positioning strap can, in this instance, be used as a secondary baffle to further protect the crotch area of the panties against staining.

A third embodiment differs from the other embodiments in two ways. First, the positioning 16 is firmly anchored to the baffle 12 at one end with the other end adhesively attached to the undergarment of the wearer by adhesive patch 14. Secondly, there is no restraining strap utilized and the napkin is free to move around the pivot point formed by attachment to the undergarment as well as backward and forward as in the previous embodiments due to the relative freedom of movement of positioning strap 16.

While not necessary, a restraining strap 15 may be incorporated with the single anchorage feature shown in the last embodiment. When this is done the strap 16 may be folded on itself under restraining strap 15 to orient the movement of the napkin axially as was the case with the first two embodiments.

What is claimed is:

1. A catamenial appliance comprising (i) means for positioning a sanitary napkin in a position to absorb body fluid discharge, said means adapted to be releasably securely adhered to the crotch area of a wearer's undergarment, (ii) a sanitary napkin which comprises (1) a body fluid-impermeable baffle sheet, (2) a body fluid-permeable, body facing cover and (3) a layer of body fluid absorbent material disposed therebetween, and (iii) means for securely attaching said sanitary napkin to said positioning means and for permitting constrained slideable movement of said sanitary napkin in response to wearer motion wherein said means (i) and (iii) comprise a strap adhered to said sanitary napkin (ii) and adapted to be releasably, adhesively securely adhered to the crotch area of a wearer's undergarment.

2. The catamenial appliance as defined by claim 1, said sanitary napkin comprising a low friction baffle (1) on the undergarment facing side thereof.

3. The catamenial appliance as defined by claim 2, said positioning means (i) comprising a low friction surface adopted to contact said low friction baffle (1).

4. The catamenial appliance as defined by claim 1, said means (iii) comprising a retention strap.

5. The catamenial appliance as defined by claim 4, said means (i) comprising a positioning strap.

6. The catamenial appliance as defined by claim 4, said retention strap extending laterally across the outer surface of said baffle sheet and encircling said positioning means (i).

7. The catamenial appliance as defined by claim 6, said positioning means (i) adopted to provide constrained longitudinal slideable movement of said sanitary napkin.

8. The catamenial appliance as defined by claim 1, said positioning means (i) comprising a strap provided with adhesive securing means at either or both of the end regions thereof.

* * * * *